(12) United States Patent
Ishii et al.

(10) Patent No.: US 11,266,595 B2
(45) Date of Patent: Mar. 8, 2022

(54) DEODORANT PRODUCTION METHOD AND DEODORANT

(71) Applicant: WELL STONE CO., Miyazaki (JP)

(72) Inventors: Yoichi Ishii, Miyazaki (JP); Takeshi Okamoto, Miyazaki (JP); Sayaka Ishii, Miyazaki (JP)

(73) Assignee: WELL STONE CO., Miyazaki (JP)

( * ) Notice: Subject to any disclaimer, the term of this patent is extended or adjusted under 35 U.S.C. 154(b) by 383 days.

(21) Appl. No.: 16/072,538

(22) PCT Filed: Dec. 16, 2016

(86) PCT No.: PCT/JP2016/087679
§ 371 (c)(1),
(2) Date: Jul. 25, 2018

(87) PCT Pub. No.: WO2017/134948
PCT Pub. Date: Aug. 10, 2017

(65) Prior Publication Data
US 2019/0060215 A1    Feb. 28, 2019

(30) Foreign Application Priority Data
Feb. 2, 2016    (JP) .............................. JP2016-018046

(51) Int. Cl.
| | | |
|---|---|---|
| *A61K 8/98* | (2006.01) | |
| *A61L 9/01* | (2006.01) | |
| *A61L 9/013* | (2006.01) | |
| *A61Q 15/00* | (2006.01) | |

(52) U.S. Cl.
CPC ................ *A61K 8/987* (2013.01); *A61L 9/01* (2013.01); *A61L 9/013* (2013.01); *A61Q 15/00* (2013.01); *A61K 2236/19* (2013.01); *A61K 2236/31* (2013.01); *A61K 2236/331* (2013.01)

(58) Field of Classification Search
CPC .......... B01D 53/34; A61K 8/987; A61K 8/98
See application file for complete search history.

(56) References Cited

U.S. PATENT DOCUMENTS

| 2012/0318199 A1 | 12/2012 | Kim |
| 2015/0064269 A1 | 3/2015 | Akazawa et al. |

FOREIGN PATENT DOCUMENTS

| CN | 2637485 | | 9/2004 | |
| CN | 1721057 | | 1/2006 | |
| CN | 101302408 | | 11/2008 | |
| CN | 102688745 | | 9/2012 | |
| CN | 104224846 | | 12/2014 | |
| JP | 54-10553 | | 5/1979 | |
| JP | 55-97281 | | 7/1980 | |
| JP | 63-84618 | | 4/1988 | |
| JP | 2-56216 | | 2/1990 | |
| JP | H0256216 A | * | 2/1990 | ............ B01D 53/34 |
| JP | 3-56627 | | 5/1991 | |
| JP | 5-2724 | | 1/1993 | |
| JP | 5-4020 | | 1/1993 | |
| JP | 7-242517 | | 9/1995 | |
| JP | 11-169444 | | 6/1999 | |
| WO | 2006/126797 | | 11/2006 | |

OTHER PUBLICATIONS

Extended European Search Report dated Aug. 30, 2019 in corresponding European Patent Application No. 16889431.9.
International Search Report (ISR) dated Jan. 17, 2017 in International (PCT) Application No. PCT/JP2016/087679.

* cited by examiner

*Primary Examiner* — Micah Paul Young
(74) *Attorney, Agent, or Firm* — Wenderoth, Lind & Ponack, L.L.P.

(57) ABSTRACT

Provided are: a method for producing a deodorant which is derived from earthworm castings and can be used in a liquid form; and a deodorant. The deodorant production method characterized by including a mixing step of mixing earthworm castings with water and a collecting step of collecting vaporized water generated from a mixture obtained in the mixing step to obtain a liquid; and the deodorant produced by the production method. It is preferred to further mix an organic substance together with the earthworm castings and the water in the mixing step.

8 Claims, 1 Drawing Sheet

DEODORANT PRODUCTION METHOD AND DEODORANT

TECHNICAL FIELD

The present invention relates to: a method for producing a deodorant which is derived from earthworm castings and can be used in a liquid form; and a deodorant produced by the production method.

BACKGROUND ART

As one of utilization methods for earthworm castings, a deodorant is known (see, for example, Patent Documents 1 to 3). It is believed that the odor eliminating effect of earthworm castings is brought about by the fact that earthworm castings have a porous structure like activated carbon and silica gel and therefore can adsorb and deodorize various odor components, and the fact that hydrogen sulfide, ammonia and the like can be decomposed by digestion enzymes or microorganisms contained in earthworm castings.

In recent years, there is a growing demand for liquid deodorants such as a spray type and the like. However, in the conventional deodorants utilizing earthworm castings, earthworm castings themselves are used, therefore, it has been difficult to produce liquid deodorants.

RELATED ART DOCUMENTS

Patent Documents

Patent Document 1: JPS54-10553B
Patent Document 2: JPH2-56216A
Patent Document 3: JPH5-4020A

SUMMARY OF THE INVENTION

Problems to be Solved by the Invention

In these situations, an object of the present invention is to provide: a method for producing a deodorant which is derived from earthworm castings and can be used in a liquid form; and a deodorant produced by the production method.

Means for Solving the Problems

The present inventors intensively studied to solve the above-described problems and consequently discovered that, a liquid obtained by collecting vaporized water generated upon the mixing of earthworm castings with water has an odor eliminating effect, thereby completing the present invention.

Namely, the deodorant production method according to the present invention is characterized by including: a mixing step of mixing earthworm castings with water; and a collecting step of collecting vaporized water generated from a mixture obtained in the mixing step to obtain a liquid.

In the deodorant production method according to the present invention, it is preferred to further mix an organic substance together with the earthworm castings and the water in the mixing step.

In the deodorant production method according to the present invention, it is preferred that the organic substance is a wood material.

It is preferred that the deodorant production method according to the present invention further includes a diluting step of diluting the liquid obtained by the collection of the vaporized water in the collecting step with water.

The deodorant according to the present invention is characterized by being produced by the deodorant production method.

Effects of the Invention

According to the present invention, it is possible to provide: a method for producing a deodorant which is derived from earthworm castings and can be used in a liquid form; and a deodorant produced by the production method.

MODE FOR CARRYING OUT THE INVENTION

Figure 1:
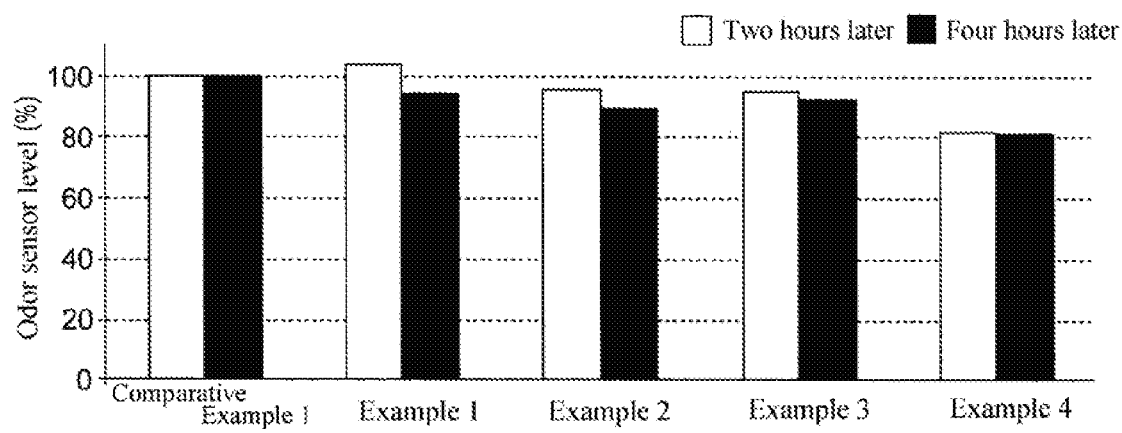
FIG. 1 is a graph illustrating the comparison of odor levels (%) among water in Comparative Example 1 and deodorants produced in Examples 1 to 4.

The deodorant production method according to the present invention is characterized by including: a mixing step of mixing earthworm castings with water; and a collecting step of collecting vaporized water generated from a mixture obtained in the mixing step. In the mixing step, it is preferred that an organic substance is further mixed together with the earthworm castings and the water. Although details about the mechanism of odor elimination is not known clearly, it is believed that microorganisms such as bacteria contained in earthworm castings decompose and ferment organic substances contained in the earthworm castings and organic substances added separately to the earthworm castings and, as a result, an odor-eliminating property is imparted to a liquid obtained by collecting the vaporized water.

Hereinbelow, the deodorant production method and the deodorant according to the present invention will be described in detail.

[Deodorant Production Method]
(Mixing Step)

The mixing step is a step of mixing earthworm castings with water.

The earthworm castings are not particularly limited, and castings of earthworms *Lumbricus rubellus*, *Lumbricus terrestris* (LT), *Eisenia foetida*, *Allolobophora caliginosa*, *Dendrobaena octaedra*, *Allolobophora japonica* Michaelsen, *Drawida hattamimizu* Hatai, *Pheretima divergens* Michaelsen, *Pheretima communissima*, *Pheretima agrestis*, *Pheretima sieboldi* Horst, *Pheretima hilgendorfi*, *Pontodrilus matsushimensis* Iizuka, *Tubifex hattai* Nomura, and *Limnodrilus gotoi* Hatai (*L. Socialis* Stephenson) can be used.

The water to be mixed with the earthworm castings is not particularly limited, and tap water and distilled water can be used. The water may be purified with a filtration material, a reverse osmosis membrane or the like. From the viewpoint of the removal of microorganisms such as bacteria, it is preferred to use a microporous filtration material, a microporous reverse osmosis membrane or the like. For example, an SPG (Shirasu porous glass) permeable membrane can be used preferably.

The mixing ratio of the earthworm castings and the water is preferably to use 0.05 to 20 L, more preferably 0.1 to 10

L, still more preferably 0.2 to 5 L, particularly preferably 0.5 to 2 L of the water with respect to 1 kg of the earthworm castings.

In the mixing step, it is preferred that an organic substance is further mixed together with the earthworm castings and the water. When an organic substance is mixed, a deodorant having superior odor eliminating effect can be produced and the pH value of the deodorant can be controlled. The organic substance is not particularly limited, as long as the organic substance can be decomposed when mixed with the earthworm castings. For example, an organic substance derived from a living organism such as an animal, a plant, a bacterium or a protozoan animal can be used. Specific examples of a plant-derived organic substance include: a wood material such as wood chips, wood dusts and rice hulls; a mushroom bed for use in the culturing of mushrooms; and the like. To mix a wood material as the organic substance is preferred, because an odorless liquid is likely be collected in the collection step. As the wood material, wood chips are preferred.

The mixing ratio of the earthworm castings and the organic substance, it is preferably to use 0.05 to 20 kg, more preferably 0.1 to 10 kg, still more preferably 0.2 to 5 kg, particularly preferably 0.5 to 2 kg of the organic substance with respect to 1 kg of the earthworm castings.

The mixing method to be employed in the mixing step is not particularly limited, and it is preferred that the mixture is fully mixed by stirring or the like. The order in which the components are mixed is not particularly limited. For example, it is possible to introduce the earthworm castings and the organic substance into a vessel and subsequently add water thereto, and it is also possible to introduce the organic substance into a vessel, subsequently add water thereto, and subsequently add the earthworm castings thereto.

It is not necessary to mix the whole amounts of the components at once, but each of the water, the earthworm castings and/or the organic substance may be replenished in divided several portions during the mixing. To mix while replenishing is preferred, because it is possible to collect vaporized water continuously while replenishing the water that can be reduced by vaporization and the earthworm castings or the organic substance that can be reduced by decomposition.

In addition, the fermentation is further stabilized after a lapse of time from the first mixing procedure. Therefore, it is preferred to collect the vaporized water, for example, after a lapse of about 1 day to obtain a liquid having a superior odor eliminating effect. From this view point, it is preferred to collect the vaporized water continuously while replenishing these components.

Heat is generated in the mixture as the result of the fermentation of the earthworm castings and the separately added organic substance. However, at some air temperatures, it is preferred to mix the components while warming. The warming may be carried out, for example, at 30 to 50° C.

(Collecting Step)

The collecting step is a step of collecting vaporized water generated from the mixture obtained in the mixing step to obtain a liquid (also referred to as "an aqueous organic substance decomposition product", hereinafter). The collecting step may be carried out while carrying out the mixing step.

In the collecting step, vaporized water generated in a temperature range rising due to a fermentation heat (reaction heat) generated as a result of the fermentation of the mixture can be collected, and it is not necessary to heat the mixture up to the boiling point. Depending on the temperatures, it is preferred to mix the components while warming. The warming may be carried out, for example, at 30° C. to 50° C.

The method for the collecting is not particularly limited, as long as vaporized water can be collected. For example, vaporized water may be collected with a dehumidifier. As the dehumidifier, a cooling-mode dehumidifier, a compression-mode dehumidifier or the like can be used. It is preferred to collect vaporized water without boiling the mixture.

The method for the conversion of the collected vaporized water to a liquid is not particularly limited. For example, when the vaporized water is collected with a dehumidifier, an aqueous organic substance decomposition product can be obtained. The dehumidifier is not particularly limited, as long as the vaporized water can be collected in a liquid form. For example, a cooling-mode dehumidifier, a compression-mode dehumidifier or the like can be used.

The pH value of the liquid obtained by the collection of the vaporized water is preferably 5 to 9, more preferably 6 to 8, still more preferably 6.5 to 7.5.

(Diluting Step)

The aqueous organic substance decomposition product obtained by the collection of the vaporized water in the collecting step may be used as a deodorant without any modification. However, it is preferred to use the aqueous organic substance decomposition product in a diluted form. The solvent to be used for the dilution may be water, and tap water and distilled water can be used. The water to be used for the dilution may be purified with a filtration material, a reverse osmosis membrane and the like. From the viewpoint of the removal of microorganisms such as bacteria, it is preferred to use a microporous filtration material, a microporous reverse osmosis membrane or the like, and an SPG (Shirasu porous glass) permeable membrane is preferably used.

In the case where the aqueous organic substance decomposition product is diluted, the dilution may be carried out at a dilution factor of, for example, 1.5 to 10 folds, preferably 4 to 6 folds, more preferably 4.5 to 5.5 folds.

[Deodorant]

The deodorant according to the present invention is characterized by being produced by the deodorant production method according to the present invention. The deodorant according to the present invention is not particularly limited, as long as the deodorant comprises a liquid produced by the deodorant production method according to the present invention and capable of exhibiting an odor eliminating effect. The deodorant is preferably in a liquid form. Alternatively, the deodorant may be a solid product having, for example, a gel-like, powdery or granular form which is prepared by mixing, for example, an excipient or the like with the liquid having the odor eliminating effect.

In the deodorant according to the present invention, other deodorant components and known conventional additives usable in deodorants (e.g., a coloring agent, a fragrance, an antioxidant agent, an ultraviolet ray absorber, a chelating agent, a surfactant, a viscosity modifier, a pH modifier, a thickening agent, an antifoaming agent, a preservative agent, an bactericidal/antibacterial agent, a dispersant and an organic solvent) may be added, as long as the advantageous effects of the present invention cannot be deteriorated.

In the deodorant according to the present invention, it is also possible to add a component capable of exhibiting an additional effect other than the odor eliminating effect to impart the additional effect to the deodorant. As such a component, an earthworm extract may be added. As the earthworm extract, an extract produced by extracting a dried earthworm powder with water, ethanol or an aqueous ethanol solution can be used, for example.

EXAMPLES

Hereinbelow, the present invention will be described more specifically with reference to Examples. However, the present invention is not intended to be limited by the following Examples. In the following Examples, "percent (%)" is by mass unless otherwise specified. In the following examples, the water used was water prepared by purifying tap water with an SPG (Shirasu porous glass) permeable membrane (SPG Technology Co., Ltd.) and activated carbon.

Example 1

Forty liters of water was introduced into a vessel containing 40 kg of earthworm *Lumbricus rubellus* castings (wherein the vessel is referred to as a "reaction vessel", hereinbelow), then vaporized water was collected by a dehumidifier (DM-30, manufactured by Nakatomi Corporation) attached to the reaction vessel for about 1 day while stirring to obtain 15 to 20 L of a liquid. Ten to twenty liters of water was further added to the reaction vessel, and vaporized water was collected by the dehumidifier for about 1 day in the same manner to obtain 15 to 20 L of a liquid. About 40 L of a liquid (pH 6.8) prepared by mixing the obtained liquids was used as a deodorant of Example 1.

Example 2

Forty liters of water was introduced into a reaction vessel containing 40 kg of earthworm *Lumbricus rubellus* castings and 15 kg of a wood material (5 kg of woodchips and 10 kg of a blend of wood dusts and rice hulls), and then vaporized water was collected by a dehumidifier (DM-30, manufactured by Nakatomi Corporation) attached to the reaction vessel for about 1 day while stirring to obtain 15 to 20 L of a liquid. Ten to twenty liters of water was further added to the reaction vessel, then 10 kg of a wood material (5 kg of woodchips and 5 kg of a blend of wood dusts and rice hulls) was added thereto, and then vaporized water was collected by the dehumidifier for about 1 day in the same manner to obtain 15 to 20 L of a liquid. About 40 L of a liquid (pH 8.71) prepared by mixing the obtained liquids was used as a deodorant of Example 2.

Example 3

Forty liters of water was introduced into a reaction vessel containing 40 kg of earthworm *Lumbricus rubellus* castings, 5 kg of a mushroom bed and 15 kg of a wood material (5 kg of woodchips and 10 kg of a blend of wood dusts and rice hulls), and then vaporized water was collected by a dehumidifier (DM-30, manufactured by Nakatomi Corporation) attached to the reaction vessel for about 1 day while stirring to obtain 15 to 20 L of a liquid (pH 8.27). The obtained liquid was used as a deodorant of Example 3.

Example 4

Forty liters of water was introduced into a reaction vessel containing 40 kg of earthworm *Lumbricus rubellus* castings, 5 kg of a mushroom bed and 15 kg of a wood material (5 kg of woodchips and 10 kg of a blend of wood dusts and rice hulls), then the resultant mixture was allowed to leave for 1 day while stirring, and then vaporized water was collected by a dehumidifier (DM-30, manufactured by Nakatomi Corporation) attached to the reaction vessel for about 1 day to obtain 15 to 20 L of a liquid (pH 7.78). The obtained liquid was used as a deodorant of Example 4.

Examples 5 to 8

The deodorants of Examples 1 to 4 were separately diluted five folds with water. The resultant liquids were used as deodorants of Examples 5 to 8, respectively.

(Evaluation of Odor Eliminating Property)

Figure 2:
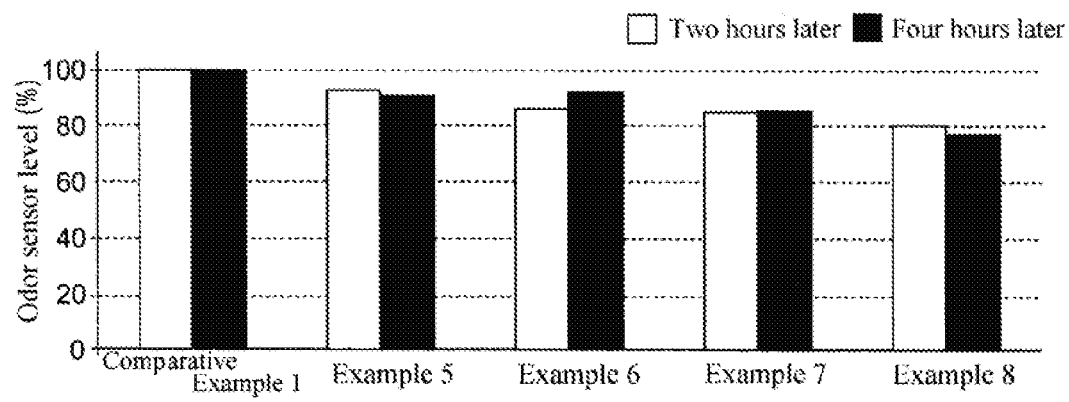
FIG. 2 is a graph illustrating the comparison of odor levels (%) among water in Comparative Example 1 and deodorants produced in Examples 5 to 8.

Into a 15-mL centrifuge tube was introduced 1.8 mL of each of the deodorants of the examples and 0.2 mL of 11% aqueous ammonia that served as an odor source or 0.2 mL of distilled water that served as a comparison. The respective resultant solution was stirred and then stored at 30° C., and then the odor of a gas phase was measured with an odor sensor XP329-IIIR (manufactured by New Cosmos Electric Co., Ltd.) 2 hours and 4 hours later. As a comparative test, the measurement of an odor was carried out in the same manner, except that the water was used as the deodorant (Comparative Example 1). The method for calculating a measurement value for an odor was as follows: a value for the odor of a distilled-water-added solution was subtracted from a value for the odor of an aqueous-ammonia-added solution, and a value for the odor of a void space in a measurement place was further subtracted therefrom. Values were compared in terms of odor levels, wherein the value for the odor in the comparative test (Comparative Example 1) was defined as 100%. When a value was smaller than 100%, it was determined that the elimination of odor was achieved. The results are shown in Table 1 and FIGS. 1 and 2.

TABLE 1

|  |  | Odor level | |
|---|---|---|---|
|  |  | 2 hours later | 4 hours later |
| Comparative Example 1 | water | 100.0% | 100.0% |
| Example 1 | deodorant (water + earthworm castings) | 103.6% | 94.4% |
| Example 2 | deodorant (water + earthworm castings + wood material) | 95.7% | 89.3% |
| Example 3 | deodorant (water + earthworm castings + wood material + mushroom bed) | 95.1% | 92.8% |

TABLE 1-continued

|  |  | Odor level | |
| --- | --- | --- | --- |
|  |  | 2 hours later | 4 hours later |
| Example 4 | deodorant (water + earthworm castings + wood material + mushroom bed) lapse of 1 day | 81.8% | 81.1% |
| Example 5 | deodorant (water + earthworm castings) 5-fold dilution | 92.7% | 91.2% |
| Example 6 | deodorant (water + earthworm castings + wood material) 5-fold dilution | 86.3% | 92.3% |
| Example 7 | deodorant (water + earthworm castings + wood material + mushroom bed) 5-fold dilution | 85.1% | 85.8% |
| Example 8 | deodorant (water + earthworm castings + wood material + mushroom bed) lapse of 1 day, 5-fold dilution | 80.5% | 77.6% |

As shown in Examples 1 to 8, it is demonstrated that a deodorant can be produced by collecting vaporized water generated from a mixture of earthworm castings and water.

The invention claimed is:

1. A method of producing a deodorant comprising:
a mixing step of mixing earthworm castings with water to obtain a mixture; and
a collecting step of vaporizing water from the mixture to generate a vaporized water and collecting the vaporized water with a dehumidifier to obtain a liquid as the deodorant.

2. The method according to claim 1, wherein the mixing step further comprises mixing an organic substance together with the earthworm castings and the water.

3. The method according to claim 2, wherein the organic substance is a wood material.

4. The method according to claim 1, further comprising a diluting step of diluting the liquid obtained in the collecting step with water to obtain the deodorant.

5. A deodorant produced by the method according to claim 1.

6. A deodorant produced by the method according to claim 2.

7. A deodorant produced by the method according to claim 3.

8. A deodorant produced by the method according to claim 4.

* * * * *